United States Patent [19]

Ison

[11] 4,275,215
[45] Jun. 23, 1981

[54] PROCESS FOR PREPARING 1-ARYL-2-BENZIMIDAZOLINONES

[75] Inventor: Robin R. Ison, Norfolk, England

[73] Assignee: Dow Chemical Company Limited, King's Lynn, England

[21] Appl. No.: 160,269

[22] Filed: Jun. 17, 1980

[30] Foreign Application Priority Data

May 3, 1978 [GB] United Kingdom ............... 17567/78

[51] Int. Cl.$^3$ .......................................... C07D 235/26
[52] U.S. Cl. .................................................. 548/305
[58] Field of Search ......................................... 548/305

[56] References Cited

U.S. PATENT DOCUMENTS 4,113,952  9/1978  Heyman ............................... 548/305

OTHER PUBLICATIONS

Oftedahl, M., et al., *J. Org. Chem.*, 28, 578–580 (1963).
Rosnati, L., *Gazz. Chim. ITAL.*, 86, 275–281 (1956).
Starks, C., *J. Am. Chem. Soc.*, 93, 195 (1971).

*Primary Examiner*—Richard A. Schwartz
*Attorney, Agent, or Firm*—S. Preston Jones; Ronald G. Brookens

[57] ABSTRACT

Process for preparing 1-aryl-2-benzimidazolinones by reacting a carbanilide and a hypohalite ion in a liquid, biphasic mixture in the presence of a quaternary ammonium and/or phosphonium salt.

10 Claims, No Drawings

PROCESS FOR PREPARING 1-ARYL-2-BENZIMIDAZOLINONES

BACKGROUND OF THE INVENTION

This invention relates to an improved process for preparing 1-aryl-2-benzimidazolinones. These compounds, methods for their preparation, and their utility as insecticides are known. Rosnati, *Gazz. Chim. Ital.*, 86, 275 (1956) and Oftedahl et al., *J. Org. Chem.*, 28, 578 (1963) both teach the preparation of 1-aryl-2-benzimidazolinones by reacting a carbanilide with aqueous hypochlorite ion. While this process is effective to produce benzimidazolinones, the yields from this process are generally unsatisfactory.

SUMMARY OF THE INVENTION

According to the present invention, 1-aryl-2-benzimidazolinones of the formula

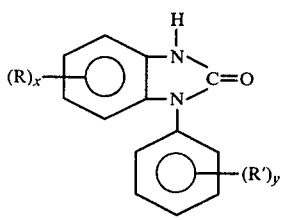

wherein R and R' are independently $C_1$–$C_4$ alkyl, alkoxy or alkylthio, fluorine, bromine or chlorine, and x and y are individually 0, 1 or 2, can be prepared by an improved process which comprises reacting by contacting:

(a) a carbanilide of the formula

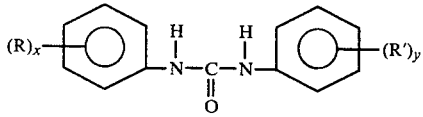

wherein R, R', x and y are defined as in (I); with (b) a hypohalite ion, in which the halogen is chlorine, bromine or iodine, as a liquid, biphasic mixture, the biphasic mixture consisting of a liquid organic phase comprising the carbanilide dissolved in an inert, organic solvent and an aqueous phase containing the hypohalite ion, the contacting is conducted in the presence of a catalytic amount of a quaternary ammonium and/or phosphonium salt. This reaction can be conducted at any temperature at which the biphasic mixture is liquid but preferably is conducted at a temperature between 15° C. and 40° C., inclusive.

The radicals of R and R', other than the stated halogens, include: methyl, ethyl, propyl, isopropyl, butyl, isobutyl, sec-butyl, methoxy, ethoxy, propoxy, methylthio, ethylthio, butylthio, etc. By "individually" is meant that R and R' or x and y can be the same or different. When x and y are both O, R and R' are not present and the compounds of (I) and (II) are unsubstituted, i.e., the compound of (I) is 1-phenyl-2-benzimidazolinone and the compound of (II) is carbanilide.

Illustrative compounds of (I) and which can be prepared by the process of this invention include:
1-phenyl-2-benzimidazolinone
6-chloro-1-(4-chlorophenyl)-2-benzimidazolinone
6-fluoro-1-(4-fluorophenyl)-2-benzimidazolinone
6-bromo-1-(4-bromophenyl)-2-benzimidazolinone
6-chloro-1-(3,4-dichlorophenyl)-2-benzimidazolinone
6-chloro-1-(3,4-dibromophenyl)-2-benzimidazolinone
6-chloro-1-(3,4-difluorophenyl)-2-benzimidazolinone
6-chloro-1-(3-bromo-4-chlorophenyl)-2-benzimidazolinone
6-bromo-1-(3,4-dibromophenyl)-2-benzimidazolinone
6-methyl-1-(4-methylphenyl)-2-benzimidazolinone
6-propyl-1-(4-propylmethyl)-2-benzimidazolinone
6-isobutyl-1-(4-isobutylphenyl)-2-benzimidazolinone
6-methyl-1-(4-ethylphenyl)-2-benzimidazolinone
6-methoxy-1-(4-methoxyphenyl)-2-benzimidazolinone
6-butoxy-1-(4-butoxyphenyl)-2-benzimidazolinone
6-methoxy-(3-methoxy-4-ethoxyphenyl)-2-benzimidazolinone
6-methylthio-1-(4-methylthiophenyl)-2-benzimidazolinone
6-propylthio-1-(4-methylthiophenyl)-2-benzimidazolinone
6-methyl-1-(4-methylthiophenyl)-2-benzimidazolinone
6-methoxy-1-(4-methylthiophenyl)-2-benzimidazolinone
6-chloro-1-(3,4-dimethylphenyl)-2-benzimidazolinone
6-ethyl-1-(3,4-dichlorophenyl)-2-benzimidazolinone
6-bromo-1-(4-methoxyphenyl)-2-benzimidazolinone
6-fluoro-1-(4-methylthiophenyl)-2-benzimidazolinone.

The carbanilide compounds of (II) useful in the practice of the present invention include:
4,4'-dichlorocarbanilide, 4,4'-difluorocarbanilide, 4,4'-dibromocarbanilide and 3,4,4'-trichlorocarbanilide.

The hypohalite ions useful in the practice of the present invention are hypochlorite, hypobromite, hypoiodite or any combination thereof. Any suitable source of hypohalite ion can be used in the practice of this invention but typically the alkali metal hypohalites are used. Due to reasons of familiarity and general availability, the hypochlorites are preferred over the other hypohalites.

The catalysts used in the practice of the present invention are quaternary ammonium and phosphonium salts and are known in the art as phasetransfer catalysts. The salts are described by Starks and Napier in British Pat. No. 1,227,144 and by Starks in the *J. Amer. Chem. Soc.*, 93, 195 (1971). Suitable salts or "onium salts" have a minimum solubility of at least about 1 weight percent in both the organic phase and the aqueous phase at 25° C. The ammonium salts are preferred over the phosphonium salts and benzyltrimethyl-, benzyltriethyl-, and tetra-n-butylammonium chlorides and bromides are most preferred.

To further illustrate the type of ammonium salts which can be used, suitable ammonium salts are represented by the formula

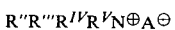

wherein R"–$R^V$ are hydrocarbyl groups, i.e., alkyl, aryl, arylalkyl or cycloalkyl, and R" can join with R''', or R''' with $R^{IV}$, to form a 5- or 6-membered heterocyclic compound having at least one quaternized nitrogen atom in the ring and may also contain one nonadjacent atom of oxygen or sulfur within the ring. Typically, R"–$R^V$ are hydrocarbyl groups of from 1 to about 16 carbon atoms each, with a combined minimum total of about 10 carbon atoms. Preferred ammonium salts have from about 10 to 30 carbon atoms. A similar formula can be drawn for the phosphonium salts.

The neutralizing anion portion of the salt, i.e., $A^{\oplus}$ in (III), may be varied to convenience. Chloride and bromide are the preferred anions, but other representative anions include fluoride, iodide, tosylate, acetate and bisulfate. The following compounds serve as a further illustration: tetra-alkyl ammonium salts, such as tetra-n-butyl-, tri-n-butylmethyl-, tetrahexyl-, trioctylmethyl-, hexadecyltriethyl-, and tridecylmethyl ammonium chlorides, bromides, iodides, bisulfates and tosylates; alkylaryl ammonium salts, such as tetrabenzyl-, benzyltrimethyl-, benzyltriethyl-, benzyltributyl-, and phenethyltrimethyl ammonium chlorides, bromides and iodides; aryl ammonium salts, such as triphenylmethyl ammonium fluoride, chloride or bromide, N,N,N-trimethylanilium chloride, N,N,N-triethylanilium bromide, N,N,N-triethylmethylanilium bisulfate, trimethylnaphthylammonium chloride, p-methylphenyltrimethylammonium chloride or tosylate; 5- and 6-membered heterocyclic compounds containing at least one quaternary nitrogen atom in the ring, such as N,N-dibutylmorpholinium chloride and N-decylthiazolium chloride; and the corresponding phosphonium salts.

Although stoichiometric amounts of oxidizable organic compound and hypohalite ion are necessary, preferably a molar excess of hypohalite ion is employed to promote a quantitative reaction. Typically, a 2- to 4-fold molar excess of hypohalite ion is used.

A catalytic amount of the onium salt is required in the practice of this invention. The concentration will vary with particular reagents employed but best results are generally achieved when the onium salt concentration is from about 1 mole percent to about 30 mole percent based upon the carbanilide. Concentrations between about 2 mole percent and about 10 mole percent are preferred.

The reaction is conducted in the presence of an inert, organic solvent. Typical solvents include benzene, chlorobenzene, o-dichlorobenzene, hexane, methylene chloride, chloroform, carbon tetrachloride, and the like. These solvents can be used alone or in combination with one another or in combination with $C_1$-$C_4$ alcohols, such as methanol and ethanol. These alcohols assist in solubilizing the carbanilides and partition well between the two phases. Not only do these inert, organic solvents contribute to the formation of a biphasic reaction mixture, but they also aid in moderating reaction rate and temperature.

Generally, at least sufficient solvent to dissolve the carbanilide is used and preferably the amount of solvent used is equal in volume to the amount of aqueous hypohalite used. Practical considerations, such as reaction vessel size, and product recovery, are the only limitations upon the maximum amount of solvent that can be used.

The carbanilides employed as starting materials are known compounds and can be prepared by any one of a number of different processes. A suitable method comprises heating under reflux an equimolar mixture of an appropriate aniline and aryl isocyanate in benzene for 1-3 hours. After cooling, crystalline product can be recovered by filtering and drying at 80° C. This process generates quantitative yields.

Important features of this invention are the use of an onium salt catalyst and contacting the carbanilide and hypohalite ion reactants as a biphasic, liquid mixture. The absence of the onium salt catalyst significantly reduces the rate of reaction and resultant yield of 1-aryl-2-benzimidazolinone. The absence of a biphasic, liquid reaction medium renders more difficult reaction control and product recovery.

In a typical embodiment of this invention, a carbanilide and onium salt catalyst are dissolved in a water-immiscible, liquid organic solvent. To this stirred mixture is added an aqueous solution of hypohalite ion, generally in a dropwise manner over an extended period of time. After all the hypohalite ion is added, the reaction mixture is continuously stirred for an additional period of time, the organic phase is separated from the aqueous phase, and the resulting product is recovered by filtering and subsequent drying.

The following examples illustrate the practice of this invention.

Control: Prior Art Preparation of 6-Chloro-1-(4-chlorophenyl)-2-benzimidazolinone A solution of sodium hydroxide (4 grams (g)) in water (15 milliliters (ml)) was added to a solution of 4,4'-dichlorocarbanilide (14.1 g, 0.05 mole) in methanol (300 ml). Sodium hypochlorite solution (100 ml, 1 N in 0.1 molar sodium hydroxide) was then added dropwise over 30 minutes to the vigorously stirred reaction mixture, maintaining the temperature below 35° C. by means of an ice bath. Stirring was continued at room temperature for 5 hours after which the small amount of solid present was removed by filtration. The filtrate was evaporated to a volume of about 50 ml, diluted with water (500 ml), and subsequently acidified to a pH of 3 with hydrochloric acid. The product was then filtered, washed with water, dried at 80° C. and identified as 6-chloro-1-(4-chlorophenyl)-2-benzimidazolinone by infrared spectra. The product recovery was 66 percent of theoretical and the product melted at 239° C. (recrystallized from toluene).

EXAMPLE 1

Onium Salt Catalyzed Preparation of 6-Chloro-1-(4-chlorophenyl)-2-benzimidazolinone 4,4'-Dichlorocarbanilide (14.1 g, 0.05 mole) and tetra-n-butyl ammonium chloride (0.7 g) were dissolved in a mixture of methylene chloride (150 ml) and methanol (150 ml). To this solution was added a solution (20 ml) of sodium hydroxide (4 g) in water and the resulting biphasic mixture was stirred vigorously before the dropwise addition of a solution of sodium hypochlorite (100 ml, 1 N in 0.1 molar sodium hydroxide) over 15 minutes. A small exotherm produced a final temperature of 33° C. The reaction mixture was then vigorously stirred for 4 hours at room temperature. Solids were removed by filtration and the biphasic system was then evaporated to a volume of about 100 ml, acidified with hydrochloric acid, and then diluted with water (500 ml). The tilted product was then recovered by filtration, dried at 80° C., and identified by infrared spectra. The product was recovered in a yield of better than 99 percent of theoretical and melted at 239° C. (recrystallized from toluene).

EXAMPLES 2–4

The procedure of Example 1 was triplicated except that various carbanilides were substituted for the 4,4'-dichlorocarbanilide and different molar scales were employed. The results are reported in Table I.

TABLE I

| Ex. | Carbanilide | Moles | 1-Aryl-2-Benzimidazolinone | Yield (%) | Melting Point (°C.) | Recrystallization Solvent |
|---|---|---|---|---|---|---|
| 2 | 4,4'-difluoro-carbanilide | 0.05 | 6-fluoro-1-(4-fluorophenyl)-2-benzimidazolinone | >99 | 223–224 | Benzene |
| 3 | 4,4'-dibromo-carbanilide | 0.075 | 6-bromo-1-(4-bromophenyl)-2-benzimidazolinone | 76 | 252 | Benzene |
| 4 | carbanilide | 0.1 | 1-phenyl-2-benzimidazolinone | 60 | 204–205 | Acetonitrile |

EXAMPLE 5

Using the procedure of Example 1, 6-chloro-1-(3,4-dichlorophenyl)-2-benzimidazolinone was prepared from 3,4,4'-trichlorocarbanilide on a 0.05 molar scale. The crude product (14.7 g, 94 percent of theoretical) melted at 220°–225° C. and consisted of 3 isomers (IV, V and VI). Recrystallization from 1:1 acetonitrile/toluene yielded the pure isomer (IV) in excess of 28 percent of theoretical with a melting point of 249°–250° C.

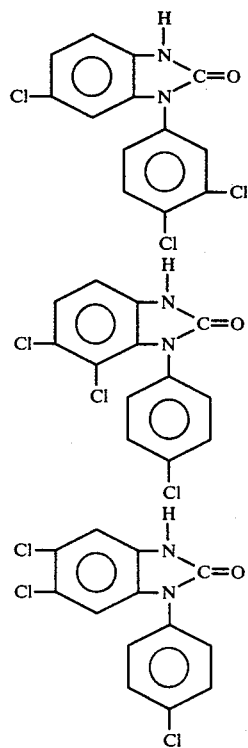

What we claim is:

1. A process for preparing 1-aryl-2-benzimidazolinones of the formula

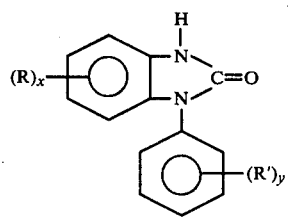

wherein
R and R' are independently $C_1$–$C_4$ alkyl, $C_1$–$C_4$ alkoxy or alkylthio, fluoro, bromo or chloro, and
x and y are individually 0, 1 or 2,
which process comprises reacting by contacting:
(a) a carbanilide of the formula

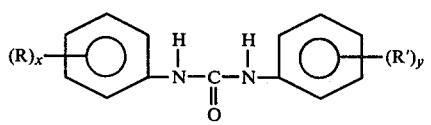

wherein R, R', x and y are defined as in (I); with
(b) a hypohalite ion, in which the halogen is chlorine, bromine or iodine,
wherein the carbanilide and hypohalite ion are contacted as a liquid, biphasic mixture, the biphasic mixture consisting of a liquid organic phase comprising the carbanilide dissolved in an inert, organic solvent and an aqueous phase containing the hypohalite ion, the contacting conducted in the presence of a catalytic amount of a quaternary ammonium and/or phosphonium salt catalyst.

2. The process of claim 1 wherein the contacting is conducted at a temperature between 15° C. and 40° C., inclusive.

3. The process of claim 2 wherein the catalyst is present in an amount of at least 1 mole percent based upon the weight of carbanilide.

4. The process of claim 3 wherein the quaternary salt is benzyltrimethyl-, benzyltriethyl-or tetra-n-butylammonium chloride or bromide.

5. The process of claim 4 wherein the hypohalite ion is hypochlorite.

6. The process of claim 5 wherein the hypochlorite ion is present in a 2 to 4 molar excess based upon the moles of carbanilide.

7. The process of claim 6 wherein the inert, organic solvent is benzene, chlorobenzene, o-dichlorobenzene, hexane, methylene chloride, chloroform or carbon tetrachloride.

8. The process of claim 6 wherein the inert, organic solvent is used in combination with a $C_1$–$C_4$ alcohol.

9. The process of claim 8 wherein R and R' are fluoride, chloride or bromide.

10. The process of claim 9 wherein x and y are each 1.

* * * * *

UNITED STATES PATENT AND TRADEMARK OFFICE
CERTIFICATE OF CORRECTION

PATENT NO. : 4,275,215
DATED : June 23, 1981
INVENTOR(S) : Robin Robert Ison

It is certified that error appears in the above—identified patent and that said Letters Patent is hereby corrected as shown below:

Column 2, line 12, reading "propylmethyl" should read -- propylphenyl --.

Column 2, line 17, before the parenthesis -1- should be inserted.

Column 2, line 44, reading "phasetransfer" should read --phase-transfer--.

Column 3, line 3, reading "$A^{\oplus}$" should read -- $A^{\ominus}$ --.

Column 4, line 58, reading "tilted" should read -- titled --.

Signed and Sealed this

First Day of December 1981

[SEAL]

Attest:

GERALD J. MOSSINGHOFF

Attesting Officer     Commissioner of Patents and Trademarks